(12) United States Patent
Knaup

(10) Patent No.: US 6,504,047 B2
(45) Date of Patent: Jan. 7, 2003

(54) 2,6-DIAMINO-6-METHYL-HEPTANOIC ACID AND DERIVATIVES, PROCESS FOR THE PREPARATION THEREOF AND USE THEREOF

(75) Inventor: Günter Knaup, Bruchköbel (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/840,977

(22) Filed: Apr. 25, 2001

(65) Prior Publication Data

US 2002/0016366 A1 Feb. 7, 2002

(30) Foreign Application Priority Data

Apr. 28, 2000 (DE) .......................... 100 20 818

(51) Int. Cl.⁷ ..................... C07C 239/00; C07C 237/00; C07C 235/00; C07C 233/00; C07C 229/00
(52) U.S. Cl. .................. 560/169; 562/561; 564/197; 564/198; 560/19
(58) Field of Search .............. 562/561; 560/169; 564/161, 169, 182, 183, 184, 192, 197, 198

(56) References Cited

FOREIGN PATENT DOCUMENTS

| EP | 0 783 002 | 7/1997 |
| WO | WO 97 38705 | 10/1997 |

OTHER PUBLICATIONS

Robl et al., "Synthetic routes for the generation of 7,7–dialkyl azepin–2–ones", Tetrahedron Letters, vol. 37, No. 50, 1996, p. 8985–8988.

Robl et al., "Vasopeptidase inhibitors: Incorporation of geminal and spirocyclic substituted azepinones in Mercaptoacyl dipeptides", J. Med. Chem., vol. 42, No. 2, 1999, p. 305–311.

Deboves et al., "A new route to hydrophobic amino acids using copper–promoted reactions of serine–derived organozinc reagents", Perkin 1, No. 24, 2000, p. 4284–4292.

Pereyra et al., "Maturation analysis in connective tissue proteins by carbon–14–labeled cyanide incorporation", J. Biol. Chem., vol. 249, No. 7, 1974, p. 2212–2219.

Salcedo et al., "Biosynthesis and stability of the aldol condensation product of α–aminoadipic acid–δ–semialdehyde", Biochem. Biophys. Acta., vol. 188, No. 2, 1969, p. 324–330.

Snowden et al., "Vitreous structure. VI. Age–related changes in the thermal stability and crosslinks of vitreous, articular cartilage and tendon collagens", Biochem. Biophys. Acta, vol. 706, No. 2, 1982, p. 153–157.

Primary Examiner—Mukund J. Shah
Assistant Examiner—Zach Tucker
(74) Attorney, Agent, or Firm—Pillsbury Winthrop LLP

(57) ABSTRACT

The present invention is directed towards compounds of the general formula (I)

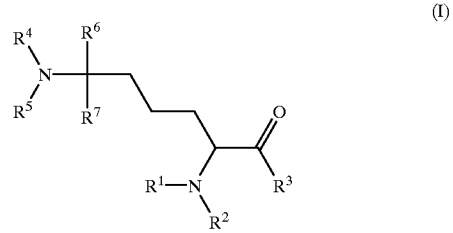

(I) are important intermediates for the preparation of pharmaceuticals.

Further intermediates, process for the preparation of (I) and use thereof.

7 Claims, No Drawings

2,6-DIAMINO-6-METHYL-HEPTANOIC ACID AND DERIVATIVES, PROCESS FOR THE PREPARATION THEREOF AND USE THEREOF

The present invention is directed towards compounds of the general formula (I)

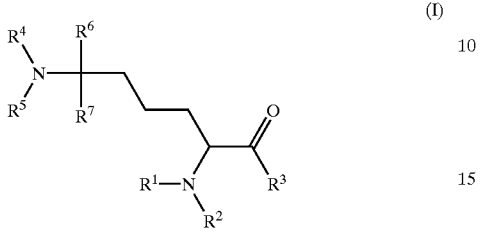

(I)

The invention also describes intermediates of (I), a process for the preparation thereof and the use thereof.

Compounds of formula (I) are suitable intermediates for the preparation of pharmaceuticals described in U.S. Pat. No. 5,552,397, WO 9738705 and in J. Med. Chem. 42, 305 (1999).

In J. Med. Chem. 42, 305 (1999), a synthesis route for the preparation of a structural unit—an α-amino-ε-caprolactam derivative—of the pharmaceutically active compounds is mentioned. That structural unit is obtained with the aid of expensive reagents in a process that is rather disadvantageous for a robust commercial process.

Accordingly, the object was to provide other precursors for the preparation of α-amino-ε-caprolactam derivatives, and to provide a process for the preparation thereof. In particular, the process is to be suitable for use on a commercial scale, that is to say advantageous from an ecological and economic point of view.

The object is achieved by compounds of the general formula (I)

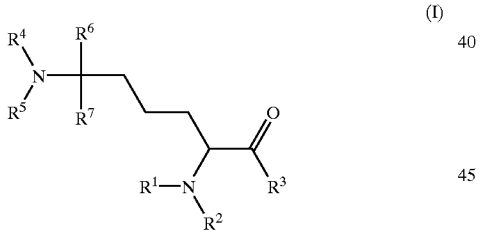

(I)

wherein $R^1$, $R^2$ each independently of the other represents H, $(C_1-C_8)$-acyl, $(C_1-C_8)$-alkoxycarbonyl, $(C_3-C_8)$-cycloalkyloxycarbonyl, $(C_6-C_{18})$-aryloxycarbonyl, $(C_7-C_{19})$-aralkyloxycarbonyl, $(C_3-C_{18})$-heteroaryloxycarbonyl, $(C_4-C_{19})$-heteroaralkyloxycarbonyl, $(C_3-C_8)$-cycloalkylcarbonyl, $(C_6-C_{18})$-arylcarbonyl, $(C_7-C_{19})$-aralkylcarbonyl, $(C_3-C_{18})$-heteroarylcarbonyl, $(C_4-C_{19})$-heteroaralkylcarbonyl, $((C_1-C_8)$-alkyl$)_{1-3}$-$(C_3-C_8)$-cycloalkyloxycarbonyl, $((C_1-C_8)$-alkyl$)_{1-3}$-$(C_6-C_{18})$-aryloxycarbonyl, $((C_1-C_8)$-alkyl$)_{1-3}$-$(C_3-C_{18})$-heteroaryloxycarbonyl, $((C_1-C_8)$-alkyl$)_{1-3}$-$(C_3-C_8$-cycloalkylcarbonyl, $((C_1-C_8)$-alkyl$)_{1-3}$-$(C_6-C_{18})$-arylcarbonyl, $((C_1-C_8)$-alkyl$)_{1-3}$-$(C_3-C_{18})$-heteroarylcarbonyl, or an N-protecting group, such as, for example, formyl, Fmoc, t-Boc, Z, $R^3$ represents OH, $NH_2$, O—$(C_1-C_8)$-alkyl, NH—$(C_1-C_8)$-alkyl, N$((C_1-C_8)$-alkyl$)_2$, O—$(C_3-C_8)$-cycloalkyl, NH—$(C_3-C_8)$-cycloalkyl, N$((C_3-C_8)$-cycloalkyl$)_2$, O—$(C_6-C_{18})$-aryl, NH—$(C_6-C_{18})$-aryl, N$((C_6-C_{18})$-aryl$)_2$, O—$(C_7-C_{19})$-aralkyl, NH—$(C_7-C_{19})$-aralkyl, N$((C_7-C_{19})$-aralkyl$)_2$, or $R^2$ and $R^3$ form a ring via a —CO—NH— group, $R^4$, $R^5$ each independently of the other represents H, $(C_1-C_8)$-acyl, $(C_3-C_8)$-cycloalkylcarbonyl, $(C_6-C_{18})$-arylcarbonyl, $(C_7-C_{19})$-aralkylcarbonyl, $(C_3-C_{18})$-heteroarylcarbonyl, $(C_4-C_{19})$-heteroaralkylcarbonyl, $((C_{1-C8})$-alkyl$)_{1-3}$-$(C_3-C_8)$-cycloalkylcarbonyl, $((C_1-C_8)$-alkyl$)_{1-3}$-$(C_6-C_{18})$-arylcarbonyl, $((C_1-C_8)$-alkyl$)_{1-3}$-$(C_3-C_{18})$-heteroarylcarbonyl, formyl, $R^6$, $R^7$ each independently of the other represents $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl, $((C_1-C_8)$-alkyl$)_{1-3}$-$(C_3-C_{18})$-heteroaryl, or the two radicals are bonded to one another via a $(C_1-C_8)$-alkylene bridge.

Compounds of the general formula (I) can readily be converted into the desired α-amino-ε-caprolactam derivatives by processes known to the person skilled in the art, whereby a novel approach to obtaining that class of compounds has been opened up.

Preference is given to compounds of the general formula (I) wherein $R^1$ represents H, $R^2$ represents an N-protecting group, especially t-Boc, Z, $R^3$ represents OH, $NH_2$, O—$(C_1-C_8)$-alkyl, NH—$(C_1-C_8)$-alkyl, $R^4$ represents H, $R^5$ represents $(C_1-C_8)$-acyl, $R^6$, $R^7$ represent $(C_1-C_8)$-alkyl.

Also preferred are compounds of the general formula (I) in which $R^1$, $R^2$=H, $R^3$=OH, $R^6$, $R^7$=methyl, $R^4$, $R^5$=H or $R^4$=H, $R^5$=formyl, or $R^4$=H, $R^5$=acetyl.

In a further embodiment, the invention relates to compounds of the general formula (II)

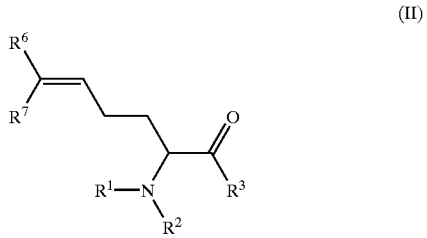

(II)

wherein $R^1$, $R^2$, $R^3$, $R^6$, $R^7$ may be as defined above. Preference is given to compounds of the general formula (II) wherein $R^1$, $R^2$=H and $R^3$=OH or $NH_2$ and $R^6$, $R^7$=methyl. Also preferred are compounds of the general formula (II) wherein $R^1$=H, $R^2$=acetyl and $R^3$=OH and $R^6$, $R^7$=methyl. Also advantageous are compounds of the general formula (II) wherein $R^1$=H and $R^2$ and $R^3$ form a ring via a —CO—NH— group, and $R^6$, $R^7$=methyl.

In another aspect, the invention is concerned with compounds of the general formula (III)

(III)

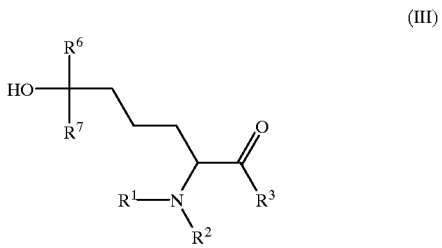

wherein $R^1$, $R^2$, $R^3$, $R^6$, $R^7$ may be as defined above, and $R^1$, $R^2$ are not phthaloyl when $R^3$=Obenzyl and $R^6$, $R^7$=methyl. Preference is given to compounds of the general formula (III) wherein $R^1$, $R^2$=H and $R^3$=OH or $NH_2$ and $R^6$, $R^7$=methyl. Also preferred are compounds of the general formula (III) wherein $R^1$=H, $R^2$=acetyl and $R^3$=OH and $R^6$, $R^7$=methyl. Also advantageous are compounds of the general formula (III) wherein $R^1$=H and $R^2$ and $R^3$ form a ring via a —CO—NH— group, and $R^6$, $R^7$=methyl.

In a further aspect, the invention is concerned with compounds of the general formula (IV)

(IV)

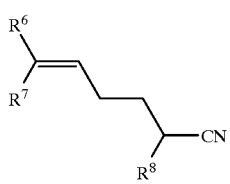

wherein $R^6$, $R^7$ may have the meanings mentioned at the beginning for those radicals and $R^8$ represents $NH_2$ or OH. $R^6$, $R^7$ preferably represent methyl.

In yet a further aspect, the invention is directed towards compounds of the general formula (V)

(V)

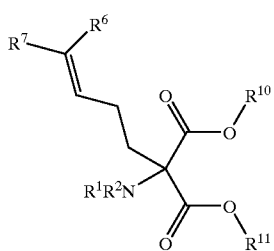

wherein
each of $R^1$, $R^2$, $R^6$, $R^7$ may be as defined at the beginning, and $R^{10}$, $R^{11}$ may represent $(C_1-C_8)$-alkyl, $(C_2-C_8)$-alkenyl, $(C_2-C_8)$-alkynyl, $(C_3-C_8)$-cycloalkyl, $(C_6-C_{18})$-aryl, $(C_7-C_{19})$-aralkyl, $(C_3-C_{18})$-heteroaryl, $(C_4-C_{19})$-heteroaralkyl, $((C_1-C_8)$-alkyl$)_{1-3}$-$(C_3-C_8)$-cycloalkyl, $((C_1-C_8)$-alkyl$)_{1-3}$-$(C_6-C_{18})$-aryl, $((C_1-C_8)$-alkyl$)_{1-3}$-$(C_3-C_{18})$-heteroaryl In (V), preferably $R^1$=H and $R^2$=acetyl and $R^{10}$, $R^{11}$=methyl or ethyl and $R^6$, $R^7$=methyl.

In a particular embodiment, the present invention relates to a process for the preparation of compounds of the general formula (I). The process is distinguished by the fact that compounds of the general formula (II) or of the general formula (III)

(II)

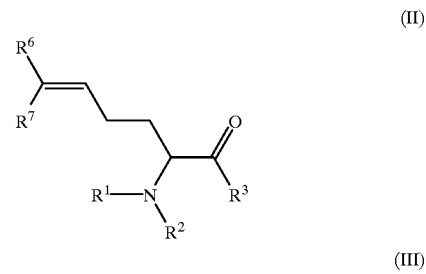

(III)

wherein $R^1$, $R^2$, $R^3$, $R^6$, $R^7$ may be as defined at the beginning, are reacted under acid conditions with a nitrile. Such a reaction, known as the Ritter reaction (Org. React. 17, 213–326 (1969)), makes it possible to obtain the substances of the general formula (I) in a high yield starting from the readily accessible compounds (II) or (III). The conditions under which the reaction takes place are in principle sufficiently well known to the person skilled in the art (Org. React. 17, 213–326 (1969)). More advantageously, however, the reaction is carried out in strongly acid media, preferably in from 65 to 85% sulfuric acid. The temperature in the reaction is on the one hand to be sufficiently high that the reaction proceeds sufficiently rapidly. On the other hand, however, it should not be chosen to be so high that the reactants are destroyed. A temperature range from −20 to 100° C. is therefore preferred, with the range from 20 to 40° C. being especially preferred. There may be used as nitrites all compounds that come into consideration to the person skilled in the art for that purpose. Preferred nitrites are those that are readily available commercially. Hydrocyanic acid, acetonitrile or benzonitrile are especially preferred. The use of hydrocyanic acid is very especially preferred. For the reaction with the nitrile, special preference is given to an N-acetyl derivative, an amide, a hydantoin of (II) or (III) or the free amino acids of (II) or (III).

The $N^6$-acyl derivatives obtained by the reaction with nitrites can be converted into the corresponding compounds having a free amino group by hydrolysis. Hydrolysis of the N-formyl compound resulting from the reaction with hydrocyanic acid proceeds in an especially simple manner. Hydrolysis of the $N^6$-acyl derivatives is preferably carried out without isolation of those compounds. To that end, the reaction mixture of the Ritter reaction is diluted with water and stirred until the acetyl compound is hydrolysed completely. The amount of water added is preferably such that a from 10 to 50% sulfuric acid solution results. The hydrolysis is preferably carried out at from 20 to 150° C., very especially preferably at from 50 to 100° C.

The $N^6$-acyl derivatives of formula (I) obtained by the reaction with nitrites may also be converted directly into the corresponding esters having a free amino group by alcoholysis. Alcoholysis of the N-formyl compound resulting from the reaction with hydrocyanic acid proceeds in an especially simple manner.

The resulting compounds of the general formula (I) can be purified by processes known to the person skilled in the art.

In the case where a free amino group is present in (I), an especially suitable method of purification is strongly acid ion-exchange chromatography. Working up of the compound (I) obtained in the Ritter reaction is preferably effected by diluting the reaction mixture with water and then applying it directly to a strongly acid ion exchanger. The sulfuric acid, which may optionally be used again after concentration, is removed by elution with water, while the amino acid is bonded to the ion exchanger. Elution with dilute ammonia then yields the pure amino acid. The advantage of that process variant is that no salt is formed, which would have to be disposed of.

It is very advantageous to generate the compounds of the general formula (II) or (III) from compounds of the general formula (IV). The chemical transformations necessary therefor are sufficiently well known to the person skilled in the art. In the case where an aminonitrile of the formula (IV) is present, it may be saponified analogously to the processes known for other amino acids either to the acid ($R^3$ in formula (II)/(III)=OH) or to the amide ($R^3$ in formula (II)/(III)=$NH_2$). Saponification to the acid can be carried out under either basic or acid conditions. Since side-reactions may optionally occur under acid conditions, it is preferably carried out under basic conditions. Saponification to the amide is preferably carried out at a pH value of from 11 to 14, preferably from 12.5 to 13.5, in the presence of a ketone, preferably acetone (EP 905257). The amide may also be prepared by known processes, for example by aminolysis of alkyl esters.

The compounds of the general formula (III) can be prepared in a very simple manner from compounds of the general formula (II) by addition of water to the double bond. That reaction preferably takes place under acid, aqueous conditions. If such conditions are used in the already described processes for the preparation of the compounds of formula (II), some or all of the corresponding compounds of the general formula (III) can be obtained immediately. It is not critical for the preparation of the compounds of formula (I) whether the alkenes of formula (II) or the alcohols of formula (III) are used for the Ritter reaction.

It is also preferred to prepare the compound of the general formula (IV) from the corresponding aldehyde by cyanide addition. Such cyanhydrin syntheses are known to the person skilled in the art. The aldehyde may also be converted directly into the aminonitrile of formula (IV) using known processes (Strecker synthesis) by reactions with cyanide compounds, such as, for example, HCN, KCN, NaCN, in the presence of ammonia. In the case of 5-methyl-4-hexenal, which is highly preferred and can be prepared in a very simple manner from 3-methyl-1-buten-3-ol and vinyl ethyl ether (R. Marbet, G. Saucy, Helv. Chimia Acta, 50, 2095 (1967)), the reaction takes place with $CN^-$ in the presence of ammonia to 6-methyl-2-amino-hept-5-enenitrile.

If the reaction of the corresponding aldehyde with hydrocyanic acid or with cyanide and ammonia is carried out in the presence of carbonate, there is obtained the hydantoin of formula (II)/(III) in which $R^1$=H, $R^2$ and $R^3$ are bonded together via a —CO—NH— group. By saponification of the hydantoin, either the amide or the acid are likewise accessible. Alternatively, the hydantoin may be prepared by reaction of the acid ($R^3$ in formula (II)/(III)=OH) with alkali cyanate, preferably potassium cyanate. If aqueous, strongly acid conditions are used for the cyclisation of the N-carbamoyl compound formed as an intermediate in that reaction, then the corresponding hydantoin of the general formula (III) is thus likewise obtained directly.

Also preferably, the compounds of the general formula (II) or (III) may also be prepared from compounds of the general formula (V). Compound of the general formula (V) may in turn be obtained by reaction of compounds of the general formula (VI)

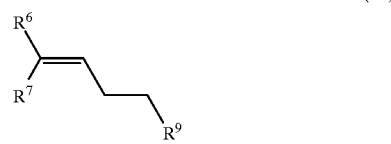

in which $R^6$, $R^7$ may be as defined at the beginning and $R^9$ represents a customary leaving group and, especially, represents halogen, $OSO_2CH_3$, —$OSO_2$—$C_6H_5$—$CH_3$, with compounds of the general formula (VII)

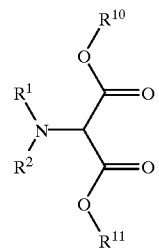

wherein $R^1$, $R^2$, $R^{10}$, $R^{11}$ may be as defined above.

That amino acid synthesis, called the malonic ester route, is well known to the person skilled in the art (Organikum, VEB-Verlag, Berlin 1986, 418). The compounds of formula (V) obtained by that reaction wherein, for example, $R^1$=H, $R^2$=acetyl, $R^{10}$, $R^{11}$=methyl can be converted into the corresponding N-acetyl-amino acids of formula (II) or (III) by saponification and subsequent decarboxylation.

The homoallyl compounds of formula (VI) that are used are preferably the halogens, which are obtainable in a simple manner, for example, by reaction of 2-cyclopropyl-2-propanol with magnesium halides (J. P. McCormick, D. L. Barton, J. Org. Chem. 45, 2566 (1980)). Very special preference is given to the use of the bromide.

Preferred malonic esters of formula (VII) that are used are acetamidomalonic esters ($R^1$=H, $R^2$=acetyl). The use of diethyl ester ($R^{10}$, $R^{11}$=ethyl) is very especially preferred.

Moreover, the N-acetyl-amino acids of formula (II) or (III) can also in principle be prepared directly from the corresponding aldehydes by amidocarbonylation (EP 338330, Angew. Chem., 109, 1534 (1997)).

In a further embodiment, the invention is concerned with the use of the compounds of the general formulae I, II, III, IV and V in the preparation of biologically active compounds. In particular, those compounds are used preferably in the preparation of α-amino-ε-caprolactam derivatives.

As described in J. Med. Chem. 42, 305 (1999), that may be effected, for example, by cyclisation of the phthaloylprotected benzyl ester. According to the present invention it is also possible in a simple manner to use for the cyclisation also other protected derivatives of formula I, such as, for example, Z, Boc, Fmoc.

It is also possible to convert the aminonitriles of formula (IV) directly into the corresponding α-amino-ε-caprolactam derivatives, for example by an intramolecular Ritter reaction.

α-Amino-ε-caprolactam derivatives may also be obtained directly from the amides of formula (II) or of formula (III), in which, preferably, $R^3$ represents $NH_2$, NH—($C_1$–$C_8$)- alkyl, NH—$(C_3–C_8)$-cycloalkyl, NH—$(C_6–C_{18})$-aryl, NH—$(C_7–C_{19})$-aralkyl or $R^2$ and $R^3$ form a ring via a —CO—NH— group, for example by reaction under strongly acid conditions (Ritter conditions).

The chemical structures indicated relate to all possible stereoisomers that can be achieved by changing the configuration of the individual chiral centres, axes or planes, that is to say all possible diastereoisomers, as well as all optical isomers (enantiomers) included therein, and also diastereoisomeric mixtures and racemates. Within the scope of the invention, however, it is very especially preferred to prepare the compounds of formula (I) in as high an enantiomerically concentrated form as possible. The L-configuration is especially preferred. Accordingly, the person skilled in the art is free to use the agents for enantiomeric separation or chiral induction that are known to him and are suitable for that purpose. The person skilled in the art is also free to decide at which stage the enantiomeric concentration is to be achieved. Preferably, however, it will take place as early in the synthesis as possible so that, optionally, inexpensively prepared wrong enantiomer does not have to be disposed of or, in the case where racemisation may be possible, losses in yield do not have to be reckoned with. It depends on each individual case, however.

Enantiomeric separation may preferably be realised either by crystallisation or with the aid of enzymes. Enzymatic processes are especially preferably used therefor.

Diastereoisomeric salt pairs with chiral acids or bases are preferably used for racemate cleavage by selective crystallisation (J. P. Greenstein, M. Winitz, "Chemistry of the Amino Acids, Wiley, N.Y., 1961, p. 716). For the formation of salt pairs with chiral acids there are preferably used the esters ($R^3$=O—$(C_1–C_8)$-alkyl, O—$(C_3–C_8)$-cycloalkyl, O—$(C_6–C_{18})$-aryl, O—$(C_7–C_{19})$-aralkyl) or the amides ($R^3$=$NH_2$) of the compounds of formula (I), (II) and (III) in which $R^1$, $R^2$=H. The formation of salt pairs with chiral bases is preferably carried out with the N-acyl compounds of formula (I), (II) and (III) in which $R^3$=OH.

A further possible method of racemate cleavage consists in separating suitable derivatives of the amino acid derivatives of formula (I), (II) or (III) by fractional crystallisation (J. P. Greenstein, M. Winitz, "Chemistry of the Amino Acids, Wiley, N.Y., 1961, p. 715).

For enzymatic racemate cleavage, the esters of (I), (II) or (III) ($R^3$ in formula (I), (II) or (III)=O—$(C_1–C_8)$-alkyl, O—$(C_3–C_8)$-cycloalkyl, O—$(C_6–C_{18})$-aryl, O—$(C_7–C_{19})$-aralkyl), for example, may be cleaved enantioselectively with enzymes, such as, for example, α-chymotrypsin ("Enzyme catalysis in Organic Chemistry", ed. K. Drauz, H. Waldmann, V C H Weinheim, 1995, p. 198).

It is also possible to obtain the desired enantiomers in concentrated form by oxidation of the undesired enantiomers of the amino acids of formula (I), (II) or (III) in which $R^1$, $R^2$=H with the aid of amino acid oxidases ("Enzyme catalysis in Organic Chemistry", ed. K. Drauz, H. Waldmann, VCH Weinheim, 1995, p. 774) to the corresponding keto acid.

A further possible method of preparing both the L- and the D-enantiomers consists in the enzymatic cleavage of the amides ($R^3$ in formula (I) (II) or (III)=NH2) with the aid of amidases ("Enzyme catalysis in Organic Chemistry", ed. K. Drauz, H. Waldmann, VCH Weinheim, 1995, p. 379).

Enzymatic cleavage of the hydantoins ($R^2$, $R^3$ in formula (I), (II) or (III) together form a —CO—NH— ring) with D- or L-hydantoinase also yields, after hydrolysis of the resulting N-carbamoyl compounds, the enantiomerically pure amino acids of formula (I), (II) or (III) ("Enzyme catalysis in Organic Chemistry", ed. K. Drauz, H. Waldmann, VCH Weinheim, 1995, p. 409).

It is also possible to cleave the N-acylamino acids of formula (I), (II) or (III) ($R^3$, $R^1$=H, $R^2$=acyl) with acylases ("Enzyme catalysis in Organic Chemistry", ed. K. Drauz, H. Waldmann, VCH Weinheim, 1995, p. 393).

Enantiomerically concentrated compounds of formula (I) or (II) can be obtained by enantioselective hydrolysis of the aminonitriles of formula (IV) with nitrilases or nitrile hydratases ("Enzyme catalysis in Organic Chemistry", ed. K. Drauz, H. Waldmann, VCH Weinheim, 1995, p. 367).

A possible method of shaping the enantioselectivity by chiral induction consists in the addition of cyanide to the corresponding aldehyde in order to obtain (IV) enantioselectively, for example with the aid of oxynitrilases ("Enzyme catalysis in Organic Chemistry", ed. K. Drauz, H. Waldmann, VCH Weinheim, 1995, p. 591) or with the aid of chiral catalysts (e.g. diketopiperazines (M. North, Synlett, 1993, 807)). The enantiomerically concentrated cyanhydrins of formula (IV) so obtainable can be converted stereoselectively into the corresponding aminonitriles ("Enzyme catalysis in Organic Chemistry", ed. K. Drauz, H. Waldmann, VCH Weinheim, 1995, p. 585).

The malonic esters of formula (V) can also be converted into the enantiomerically concentrated amino acid derivatives of formula (II) or (III) by enzymatic partial hydrolysis analogously to the process described in EP 812819.

The L-amino acids of formula (I) required for the preparation of the intermediates described in U.S. Pat. No. 5,552, 397, WO 9738705 and in J. Med. Chem. 42, 305 (1999) are preferably prepared by enzymatic cleavage of the N-acylamino acids. The cleavage may be carried out, for example, either with 2,6-diamino-6-methylheptanoic acids or with 2-amino-6-methyl-5-heptenoic acids or 2-amino-6-hydroxy-6-methyl-heptanoic acids. The latter can be converted into the former by the reaction with nitrites according to the invention without any loss in optical purity.

There are preferably used for the acylase cleavage the N-acetylamino acids of formula (I) or (II). The acylase cleavage may be carried out, for example, either with the $N^6$-acyl compounds resulting from the Ritter reaction or with the corresponding $N^6$-deprotected compounds. Very special preference is given to the use of the $N^2$-acetylamino acids of formula (II) for the acylase cleavage.

The enzyme preferably used is an L-acylase, and the reaction is carried out at a pH value of from 3 to 9, preferably from 5 to 8. There are preferably used as base alkali metal hydroxides, very especially preferably sodium hydroxide.

Advantageously, in the case of N-acyl-2-amino-6-methyl-5-heptenoic acid, 2-amino-6-methyl-5-heptenoic acid precipitates from the reaction medium after the acylase cleavage and can be separated off in a simple manner by filtration.

Otherwise, the L-amino acids are separated from the unreacted D-acylamino acids preferably by chromatography on ion exchangers. A strongly acid ion exchanger is preferably used for that purpose. In that case, the amino acid and the cations of the base that is used are bonded, while the acylamino acids and the carboxylic acids corresponding to the acyl group can be washed out with water. The amino acid can then be eluted selectively, for example with aqueous ammonia.

The undesired enantiomers formed in the enantiomeric separation can be racemised by known processes and used again (e.g. racemisation of amides: EP 905257, EP 442585; racemisation of N-acetylamino acids U.S. Pat. No. 4,602, 096).

$(C_1–C_8)$-Alkyl may be regarded as being methyl, ethyl, n-propyl, isopropyl, n-butyl, isobutyl, sec-butyl, tert-butyl, pentyl, hexyl, heptyl or octyl, including all isomers due to different positions of the double bond. They may be mono- or poly-substituted by $(C_1-C_8)$-alkoxy, $(C_1-C_8)$-haloalkyl, OH, halogen, $NH_2$, $NO_2$, SH, S—$(C_1-C_8)$-alkyl.

$(C_2-C_8)$-Alkenyl is to be understood as being a $(C_1-C_8)$-alkyl radical as described above, with the exception of methyl, that has at least one double bond.

$(C_2-C_8)$-Alkynyl is to be understood as being a $(C_1-C_8)$-alkyl radical as described above, with the exception of methyl, that has at least one triple bond.

$(C_1-C_8)$-Acyl is to be understood as being a $(C_1-C_8)$-alkyl radical bonded to the molecule via a —C=O— function.

$(C_3-C_8)$-Cycloalkyl is to be understood as being cyclopropyl, cyclobutyl, cyclopentyl, cyclohexyl and cycloheptyl radicals, etc. They may be substituted by one or more halogens and/or radicals containing an N, O, P, S atom and/or may have in the ring radicals containing an N, O, P, S atom, such as, for example, 1-, 2-, 3-, 4-piperidyl, 1-, 2-, 3-pyrrolidinyl, 2-, 3-tetrahydrofuryl, 2-, 3-, 4-morpholinyl. They may also be mono- or poly-substituted by $(C_1-C_8)$-alkoxy, $(C_1-C_8)$-haloalkyl, OH, Cl, $NH_2$, $NO_2$.

A $(C_6-C_{18})$-aryl radical is to be understood as being an aromatic radical having from 6 to 18 carbon atoms. Such radicals include especially compounds such as phenyl, naphthyl, anthryl, phenanthryl, biphenyl radicals. It may be mono- or poly-substituted by $(C_1-C_8)$-alkoxy, $(C_1-C_8)$-haloalkyl, OH, halogen, $NH_2$, $NO_2$, SH, S—$(C_1-C_8)$-alkyl.

A $(C_7-C_{19})$-aralkyl radical is a $(C_6-C_{18})$-aryl radical bonded to the molecule via a $(C_1-C_8)$-alkyl radical.

$(C_1-C_8)$-Alkoxy is a $(C_1-C_8)$-alkyl radical bonded to the molecule in question via an oxygen atom.

$(C_1-C_8)$-Alkoxycarbonyl is a $(C_1-C_8)$-alkyl radical bonded to the molecule in question via a —OC(O)— function. The same applies synonymously to the other oxycarbonyl radicals.

$(C_1-C_8)$-Haloalkyl is a $(C_1-C_8)$-alkyl radical substituted by one or more halogen atoms.

Within the scope of the invention, a $(C_3-C_{18})$-heteroaryl radical denotes a five-, six- or seven-membered aromatic ring system of from 3 to 18 carbon atoms that contains hetero atoms such as, for example, nitrogen, oxygen or sulfur in the ring. Such heteroaromatic radicals are to be regarded as being especially radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. It may be mono- or poly-substituted by $(C_1-C_8)$-alkoxy, $(C_1-C_8)$-haloalkyl, OH, halogen, $NH_2$, $NO_2$, SH, S—$(C_1-C_8)$-alkyl.

A $(C_4-C_{19})$-heteroaralkyl is to be understood as being a heteroaromatic system corresponding to the $(C_7-C_{19})$-aralkyl radical.

The expression $(C_1-C_8)$-alkylene unit is to be understood as meaning a $(C_1-C_8)$-alkyl radical that is bonded to the molecule in question via two single bonds of its carbon atoms. It may be mono- or poly-substituted by $(C_1-C_8)$-alkoxy, $(C_1-C_8)$-haloalkyl, OH, halogen, $NH_2$, $NO_2$, SH, S—$(C_1-C_8)$-alkyl.

Suitable halogens are fluorine, chlorine, bromine and iodine.

Within the scope of the invention, the expression enantiomerically concentrated is to be understood as meaning the proportion of an enantiomer in admixture with its optical antipodes in a range >50% and <100%.

EXAMPLES

1. Preparation of D,L-1-amino-5-methyl-4-heptenylnitrile 67.76 g of sodium cyanide and 28.4 g of ammonium chloride are dissolved in 210 ml of water and 194 g of 25% aqueous ammonia solution, and heated to 60° C. 71.0 g of 5-methyl-2-hexanal are added dropwise in the course of 30 minutes, and stirring is then carried out for 1.5 hours at 60° C. Cooling and extraction with 200 ml of MtBE are then carried out. Removal of the solvent by distillation yields 77 g of the aminonitrile in the form of an oil.

$^1$H-NMR (DMSO): 1.59 (s, 3H), 1.66 (s, 3H), 2.08 (m, 3H), 2.27 (m, 2H), 3.62 (m, 1H), 5.09 (m, 1H).

MS: 139 (M+H$^+$), 112 (M−HCN+H$^+$), 95.

2. Preparation of D,L-2-amino-6-methyl-5-heptenoic Acid 696 g of 25% aqueous ammonia solution are added to 168.8 g of 5-methyl-2-hexanal, 67.76 g of sodium cyanide, 86.0 g of ammonium chloride in 510 ml of water, and the whole is heated for 2 hours at 60° C. 300 g of 50% sodium hydroxide solution are then added, and heating is carried out for 4 hours at reflux. Cooling and extraction with 500 ml of MIBK are then carried out, and the aqueous phase is concentrated to 850 g in vacuo. The pH value is adjusted to 6 using concentrated hydrochloric acid; 300 ml of acetone are added, the solid is filtered off, and washing with water and acetone are then carried out. Drying yields 89 g of D,L-2-amino-6-methyl-5-heptenoic acid.

$^1$H-NMR (DMSO+HCl): 1.58 (s, 3H), 1.66 (s, 3H), 1.81 (m, 2H), 2.02 (m, 1H), 2.12 (m, 1H), 3.82 (m, 1H), 5.04 (masked by $H_2O$, 1H), 8.50 (s, 1H).

3. Preparation of $N^6$-acetyl-D,L-2,6-diamino-6-methyl-heptanoic Acid 29.6 g of D,L-2-amino-6-methyl-5-heptenoic acid and 9.74 ml of acetonitrile are stirred for 14 hours at room temperature in 47 g of 96% sulfuric acid and 7.1 g of water. 100 g of ice and 600 ml of water are then added. The solution is applied to a column containing 600 ml of Amberlite 252 C. and washed with water. Elution with 5% ammonia yields, after concentration in vacuo and digestion with 300 ml of MIBK, 36.0 g of $N^6$-acetyl-D,L-2,6-diamino-6-methyl-heptanoic acid.

$^1$H-NMR (DMSO+HCl): 1.20 (s, 6H), 1.28 (m, 1H), 1.39 (m, 1H), 1.62 (m, 2H), 1.76 (m, 2H), 1.82 (s, 3H), 3.82 (m, 1H), 7.65 (br.s, 1H), 8.48 (br.s, 3H).

4. Preparation of N-acetyl-D,L-2-amino-6-methyl-5-heptenoic Acid 25 g of D,L-2-amino-6-methyl-5-heptenoic acid are suspended in 140 ml of water and adjusted to pH 11 using 50% sodium hydroxide solution. 18 g of acetic anhydride are then added dropwise at 20–25° C. and the pH value is maintained between 10 and 11 during the addition by addition of 50% sodium hydroxide solution. Stirring is then carried out for 15 minutes and the pH value is then adjusted to 2 using concentrated hydrochloric acid. The solid that precipitates is filtered off, washed with water and dried. 28.1 g of N-acetyl-D,L-2-amino-6-methyl-5-heptenoic acid are obtained.

$^1$H-NMR (DMSO): 1.55 (s, 3H), 1.56–1.72 (m, 2H), 1.65 (s, 3H), 1.84 (s, 3H), 1.99 (m, 2H), 4.12 (m, 1H), 5.06 (m, 1H), 8.07 (d, 1H).

5. Preparation of L-2-amino-6-methyl-5-heptenoic Acid 26.6 g of N-acetyl-D,L-2-amino-6-methyl-5-heptenoic acid are suspended in 135 ml of water, and the pH value is adjusted to 7.0 by addition of 50% sodium hydroxide solution. 0.8 g of L-acylase is then added, and stirring is carried out for 5 days at room temperature. Removal of the precipitate by filtration and washing with water yield 8.8 g of L-2-amino-6-methyl-5-heptenoic acid having a $[\alpha]_{589}^{25}$ of +32.5° (c=1, 1N HCl) and a D content (chiral GC) of <0.1%.

6. Preparation of N,N-diacetyl-L-2,6-diamino-6-methyl-heptanoic Acid 28.1 g of $N^6$-acetyl-D,L-2,6-diamino-6-methyl-heptanoic acid are dissolved in 130 ml of water and adjusted to pH 10 using 50% sodium hydroxide solution. 14.6 g of acetic anhydride and 50% sodium hydroxide solution are then added dropwise, with cooling, in such a manner that the temperature remains <30° C. and the pH value remains between 10 and 11. After stirring for a further 10 minutes, the pH value is adjusted to 7 by addition of concentrated hydrochloric acid. A sample of the solution was concentrated to dryness by evaporation in vacuo.

$^1$H-NMR (D$_2$O): 1.26 (s, 3H), 1.32 (m, 2H), 1.66 (m, 3H), 1.75 (m, 1H), 1.92 (s, 3H), 2.03 (s, 3H), 4.12 (m, 1H).

7. Preparation of $N^6$-acetyl-L-2,6-diamino-6-methyl-heptanoic Acid a) From L-2-amino-6-methyl-5-heptenoic Acid 8.3 g of the L-2-amino-6-methyl-5-heptenoic acid from Experiment 6 are reacted analogously to Test 3 with 13.2 g of 96% sulfuric acid, 2.0 g of water and 2.8 ml of acetonitrile. 11.5 g of $N^6$-acetyl-L-2,6-diamino-6-methyl-heptanoic acid having a $[\alpha]_{589}^{25}$ of +20.7° (c=1, 1N HCl) and a D content (chiral HPLC) of <0.2% are obtained.

b) By Acylase Cleavage of N,N-diacetyl-L-2,6-diamino-6-methyl-heptanoic Acid

The aqueous solution from Experiment 6 is made up to 300 ml with water; 2.0 g of L-acylase are added thereto and stirring is carried out for 4 days at room temperature. The solution is applied to a column containing 550 ml of Amberlite 252 C., and the unreacted N,N-diacetyl-D(L)-2,6-diamino-6-methyl-heptanoic acid is eluted with water. Concentration of the eluate in vacuo yields 48 g. Elution is then carried out with 5% ammonia. Concentration in vacuo and digestion of the solid with acetone yield 7.8 g of $N^6$-acetyl-L-2,6-diamino-6-methyl-heptanoic acid having a $[\alpha]_{589}^{25}$ of +18.0° (c=1, 1N HCl) and a D content (chiral HPLC) of 0.2%.

8. Preparation of $N^6$-formyl-L-2,6-diamino-6-methyl-heptanoic Acid 1.9 g of L-2-amino-6-methyl-5-heptenoic acid are added to a solution of 0.56 ml of hydrocyanic acid in 6.0 g of 96% sulfuric acid and 0.9 g of water, and stirring is carried out for 2 hours at room temperature. 10 g of ice are then added, and the mixture is made up to 70 ml with water. The solution is applied to a column containing 60 ml of Amberlite 252 C. and then washed with water. Elution with 5% ammonia yields, after concentration in vacuo and digestion with 30 ml of acetone, 1.9 g of $N^6$-formyl-L-2,6-diamino-6-methyl-heptanoic acid.

$^1$H-NMR (DMSO+HCl): 1.22 (s, 6H), 1.30 (m, 1H), 1.43 (m, 1H), 1.62 (m, 2H), 1.77 (m, 2H), 3.83 (m, 1H), 7.76 (s, 1H), 7.86 (br.s, 1H), 8.48 (br.s, 3H).

9. Preparation of L-2,6-diamino-6-methyl-heptanoic Acid Di-hydrochloride 1.0 g of $N^6$-formyl-L-2,6-diamino-6-methyl-heptanoic acid is heated for 2.5 hours at reflux in 10 ml of 1 N hydrochloric acid. The reaction mixture is then concentrated in vacuo and dried. 1.3 g of L-2,6-diamino-6-methyl-heptanoic acid dihydrochloride are obtained.

$^1$H-NMR (DMSO): 1.23 (s, 6H), 1.41 (m, 1H), 1.51 (m, 1H), 1.58 (m, 2H), 1.79 (m, 2H), 3.83 (m, 1H), 8.21 (br. s, 3H), 8.52 (br. s, 3H), 13.6 (br.s, 1H).

10. Preparation of D,L-2-amino-6-hydroxy-6-methyl-heptanoic Acid Hydrochloride 1.0 g of D,L-2-amino-6-methyl-5-heptenoic acid is heated for one hour at reflux in 10 ml of water and 3 ml of concentrated hydrochloric acid. The reaction mixture is then concentrated in vacuo; 20 ml of MIBK are added and concentration is again carried out. The solid that precipitates is filtered off and dried. 1.2 g of D,L-2-amino-6-hydroxy-6-methyl-heptanoic acid hydrochloride are obtained.

$^1$H-NMR (DMSO): 1.07 (s, 6H), 1.34 (m, 3H), 1.47 (m, 1H), 1.55 (s, 1H), 1.78 (m, 2H), 3.82 (m, 1H), 8.48 (br.s, 3H), 13.6 (br.s, 1H).

11. Preparation of D,L-5-(4-hydroxy-4-methyl-pentyl)-hydantoin 4.72 g of D,L-2-amino-6-methyl-5-heptenoic acid are heated for 2 hours at 70–80° C. with 1.7 g of potassium hydroxide and 3.65 g of potassium cyanate. The pH is then adjusted to 0.5 using concentrated hydrochloric acid, and stirring is carried out for one hour at room temperature. The mixture is then rendered neutral using sodium hydroxide solution, and the precipitate is filtered off and drying is carried out in vacuo. 2.90 g of D,L-5-(4-hydroxy-4-methyl-pentyl)-hydantoin are obtained.

$^1$H-NMR (DMSO): 1.06 (s, 6H), 1.33 (m, 4H), 1.49 (m, 1H), 1.62 (m, 1H), 3.98 (m, 1H), 4.07 (s, 1H), 7.90 (br.s, 1H), 10.52 (br.s, 1H).

12. Preparation of acetamido-(4-methyl-3-pentenyl)-malonic Acid Diethyl Ester 27.1 g of acetamidomalonic acid diethyl ester are heated for 14 hours with 19.6 g of 5-bromo-2-methyl-2-pentene and 16.6 g of potassium carbonate in 100 ml of MIBK in a water separator. The reaction solution was extracted with 100 ml of water, and the organic phase was concentrated in vacuo. LC-MS analysis of the residue shows that it is a mixture of N-acetyl-D,L-2-amino-6-methyl-5-heptenoic acid ethyl ester (M+H$^+$=228) and acetamido-(4-methyl-3-pentenyl)-malonic acid diethyl ester (M+H$^+$=300) in a ratio of 3:2.

13. Preparation of N-acetyl-D,L-2-amino-6-methyl-5-heptenoic acid from acetamido-(4-methyl-3-pentenyl)-malonic Acid Diethyl Ester A sample of the mixture obtained in Experiment 12 is heated for 14 hours at reflux with 10 g of 50% sodium hydroxide solution in 120 ml of water and 100 ml of ethanol. HPLC then shows that N-acetyl-D,L-2-amino-6-methyl-5-heptenoic acid has formed.

14. Cyclisation of D,L-1-amino-5-methyl-4-heptenylnitrile 0.10 g of D,L-1-amino-5-methyl-4-heptenylnitrile is stirred for 14 hours in 0.32 g of 96% sulfuric acid and 0.05 g of water. LC-MS analysis of the reaction mixture diluted with water shows for the main peak an MS with 157 (M+H$^+$) and 112.

15. Cyclisation of D,L-5-(4-hydroxy-4-methyl-pentyl)-hydantoin 1.6 g of D,L-5-(4-hydroxy-4-methyl-pentyl)-hydantoin are stirred for 14 hours at room temperature with 0.42 ml of acetonitrile in 4.0 g of 96% sulfuric acid and 0.6 g of water. 20 ml of water are then added, and the pH value is adjusted to 7 using 50% sodium hydroxide solution. The solid that precipitates is filtered off and dried. 0.51 g of 2,2-dimethyl-1,7-diaza-bicyclo[4,2,1]nonane-1,7-dione is obtained.

$^1$H-NMR (DMSO): 1.22 (s, 3H); 1.27 (m, 1H), 1.39 (m, 1H), 1.50 (m, 1H), 1.57 (s, 3H), 1.64 (m, 2H), 1.95 (m, 1H), 4.03 (dd, 1H), 10.44 (br.s, 1H).

16. Preparation of L-2,6-diamino-6-methyl-heptanoic Acid Methyl Ester Dihydrochloride 0.5 g of $N^6$-formyl-L-2,6-diamino-6-methyl-heptanoic acid is stirred for 14 hours at room temperature in 10 ml of methanol with 0.45 g of thionyl chloride and then heated for 2 hours at 60° C. Concentration of the reaction mixture and drying of the residue in vacuo yield 0.65 g of L-2,6-diamino-6-methyl-heptanoic acid methyl ester dihydrochloride.

What is claimed is:

1. Compounds of the general formula (I)

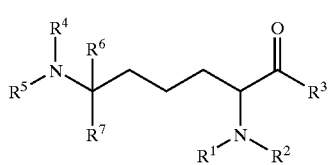

(I)

wherein

R$^1$, R$^2$ each independently of the other represents H, (C$_1$–C$_8$)-acyl, (C$_1$–C$_8$)-alkoxycarbonyl, (C$_3$–C$_8$)-cycloalkyloxycarbonyl, (C$_6$–C$_{18}$)-aryloxycarbonyl, (C$_7$–C$_{19}$)-aralkyloxycarbonyl, (C$_3$–C$_{18}$)-heteroaryloxycarbonyl, (C$_4$–C$_{19}$)-heteroaralkyloxycarbonyl, (C$_3$–C$_8$)-cycloalkylcarbonyl, (C$_6$–C$_{18}$)-arylcarbonyl, (C$_7$–C$_{19}$)-aralkylcarbonyl, (C$_3$–C$_{18}$)-heteroarylcarbonyl, (C$_4$–C$_{19}$)-heteroaralkylcarbonyl, ((C$_1$–C$_8$)-alkyl )$_{1-3}$-(C$_3$–C$_8$)-cycloalkyloxycarbonyl, ((C$_1$–C$_8$)-alkyl)$_{1-3}$-(C$_6$–C$_{18}$)-aryloxycarbonyl, ((C$_1$–C$_8$)-alkyl)$_{1-3}$-(C$_3$–C$_{18}$)-heteroaryloxycarbonyl, ((C$_1$–C$_8$)-alkyl)-$_{1-3}$-(C$_3$–C$_8$)-cycloalkylcarbonyl, ((C$_1$–C$_8$)-alkyl)$_{1-3}$-(C$_6$–C$_{18}$)-arylcarbonyl, ((C$_1$–C$_8$)-alkyl)$_{1-3}$-(C$_3$–C$_{18}$)-heteroarylcarbonyl, formyl, Fmoc, t-Boc, or benzyloxycarbonyl;

R$^3$ represents OH, NH$_2$, O—(C$_1$–C$_8$)-alkyl, NH—(C$_1$–C$_8$)-alkyl, N((C$_1$–C$_8$)-alkyl)$_2$, O—(C$_3$–C$_8$)-cycloalkyl, NH—(C$_3$–C$_8$)-cycloalkyl, N((C$_3$–C$_8$)-cycloalkyl)$_2$, O—(C$_6$–C$_{18}$)aryl , NH—(C$_6$–C$_{18}$)-aryl, N((C$_6$–C$_{18}$)-aryl)$_2$, O—(C$_7$–C$_{19}$)-aralkyl , NH—(C$_7$–C$_{19}$)-aralkyl , N((C$_7$–C$_{19}$)-aralkyl)$_2$, or R$^2$ and R$^3$ form a hydantoine ring, R$^4$, R$^5$ each independently of the other represents H, (C$_1$–C$_8$)-acyl, (C$_3$–C$_8$)-cycloalkylcarbonyl, (C$_6$–C$_{18}$)-arylcarbonyl, (C$_7$–C$_{19}$)-aralkylcarbonyl, (C$_3$–C$_{18}$)-heteroarylcarbonyl, (C$_4$–C$_{19}$)-heteroaralkylcarbonyl, ((C$_1$–C$_8$)-alkyl )$_{1-3}$-(C$_3$–C$_8$)-cycloalkylcarbonyl, ((C$_1$–C$_8$)-alkyl )$_{1-3}$-(C$_6$–C$_{18}$)-arylcarbonyl, ((C$_1$–C$_8$)-alkyl)$_{1-3}$-(C$_3$–C$_{18}$)-heteroarylcarbonyl, formyl, R$^6$, R$^7$ each independently of the other represents (C$_1$–C$_8$)-alkyl, (C$_2$–C$_8$)-alkenyl, (C$_2$–C$_8$)-alkynyl, (C$_3$–C$_8$)-cycloalkyl, (C$_6$–C$_{18}$)-aryl, (C$_7$–C$_{19}$)-aralkyl, (C$_3$–C$_{18}$)-heteroaryl, (C$_4$–C$_{19}$)-heteroaralkyl, ((C$_1$–C$_8$)-alkyl)$_{1-3}$-(C$_3$–C$_8$)-cycloalkyl, ((C$_1$–C$_8$)-alkyl)$_{1-3}$-(C$_6$–C$_{18}$)-aryl, ((C$_1$–C$_8$)-alkyl)$_{1-3}$-(C$_3$–C$_{18}$)-heteroaryl, or the two radicals are bonded to one another via a (C$_1$–C$_8$)-alkylene bridge.

2. Compounds according to claim 1, wherein

R$^1$ represents H, R$^2$ represents t-Boc or benzyloxycarbonyl,

R$^3$ represents OH, NH$_2$, O—(C$_1$–C$_8$)-alkyl, NH—(C$_1$–C$_8$)-alkyl,

R$^4$ represents H, R$^5$ represents (C$_1$–C$_8$)-acyl,

R$^6$, R$^7$ represent (C$_1$–C$_8$)-alkyl.

3. Compounds according to claim 1, in which R$^1$, R$^2$=H, R$^3$=OH, R$^6$, R$^7$=methyl, R$^4$, R$^5$=H or R$^4$=H, R$^5$=formyl, or R$^4$=H, R$^5$=acetyl.

4. Process for the preparation of compounds according to claim 1, characterised in that compounds of the general formula (II) or (III),

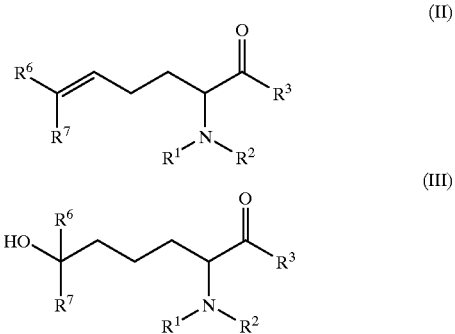

wherein R$^1$, R$^2$, R$^3$, R$^6$, R$^7$ are defined according to claim 1, and are reacted under acid conditions with a nitrile.

5. Process according to claim 4, characterised in that the reaction is carried out in from 65 to 85% sulfuric acid.

6. Process according to claim 4 or 5, characterised in that the reaction is carried out at a temperature of from 20 to 40° C.

7. Process according to claim 4 or 5, characterised in that hydrocyanic acid, acetonitrile or benzonitrile are used as the nitriles.

* * * * *